(12) United States Patent
Gildersleeve et al.

(10) Patent No.: US 11,141,303 B2
(45) Date of Patent: Oct. 12, 2021

(54) BIASED SUPPORT FOR HINGE JOINT

(71) Applicant: Nordt Development Co., LLC, Charles City, VA (US)

(72) Inventors: Richard E. Gildersleeve, Escondido, CA (US); William E. Nordt, III, Charles City, VA (US); Ian Kovacevich, Carlsbad, CA (US)

(*) Notice: Subject to any disclaimer, the term of this patent is extended or adjusted under 35 U.S.C. 154(b) by 135 days.

(21) Appl. No.: 16/411,040

(22) Filed: May 13, 2019

(65) Prior Publication Data

US 2019/0365557 A1 Dec. 5, 2019

Related U.S. Application Data

(63) Continuation of application No. 13/842,513, filed on Mar. 15, 2013, now abandoned.

(51) Int. Cl.
*A61F 5/00* (2006.01)
*A61F 5/01* (2006.01)

(52) U.S. Cl.
CPC .......... *A61F 5/0123* (2013.01); *A61F 5/0102* (2013.01)

(58) Field of Classification Search
CPC ........ A61F 5/01; A61F 5/0123; A61F 5/0102; A61F 5/0106; A61F 5/013; A61F 5/0118; A61F 2005/0132; A61F 2005/0134; A61F 2005/0137; A61F 5/0125; A61F 2005/0144; A61F 2005/0146; A61F 2005/0139; A61F 5/0109; A61F 2005/0141
USPC ..................................................... 602/16, 26
See application file for complete search history.

(56) References Cited

U.S. PATENT DOCUMENTS

| 4,803,975 A | 2/1989 | Meyers |
| 2007/0021706 A1 | 1/2007 | Braunstein et al. |
| 2009/0259156 A1 | 10/2009 | Nordt et al. |

*Primary Examiner* — Victoria J Hicks
(74) *Attorney, Agent, or Firm* — Tillman Wright, PLLC; Chad D. Tillman; Jeremy C. Doerre

(57) ABSTRACT

A support for an area of a body that includes a hinge joint includes a flexible, elastically stretchable framework comprising an integrally molded network of interconnected, elastomeric segments defining a plurality of permanent openings; a structural hinge mechanism affixed to a first side of the framework, and a secondary hinge mechanism affixed to a second side of the framework. The structural hinge mechanism is larger than the secondary hinge mechanism so as to bias the application of pressure towards one side of the hinge joint when the support is secured to the area of the body. The elastomeric segments of the framework are designed in such a way as to asymmetrically assert pressure on the hinge joint when the support is secured to the area of the body. The structural hinge mechanism and the framework work together to bias application of pressure generally in the same direction.

14 Claims, 9 Drawing Sheets

BIASED SUPPORT FOR HINGE JOINT

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to apparatus and methods for supporting a hinge joint.

Joint fatigue, pain, and instability are common conditions of active and aging people. This is especially true with regard to hinge joints of the body, including the knee joint and the elbow joint. Such joint ailments often can be attributed to damage to, and degenerative wear in, the contact surfaces of bone ends meeting at the joint. External support in these areas of the body can help address joint fatigue, pain, and/or instability and, generally, external support in various areas of the body can serve to address many different conditions. One or more aspects of the invention provide such support. Moreover, one or more aspects of the invention even augment motion about joints and, in particular, about hinge joints.

It is common for joints to deteriorate, for example a person's knee may go out of alignment as the inside space of their knee joint collapses. Unloader braces are sometimes utilized to apply pressure to the knee to try to offset this.

However, a need exists for improvement in unloader braces. This, and other needs, are addressed by one or more aspects of the present invention.

SUMMARY OF THE INVENTION

The present invention includes many aspects and features. Moreover, while many aspects and features relate to, and are described in, the context of a knee support, the present invention is not limited to use only in this context, as will become apparent from the following summaries and detailed descriptions of aspects, features, and one or more embodiments of the present invention.

Accordingly, one aspect of the present invention relates to a support for an area of a body that includes a hinge joint. The support includes a flexible, elastically stretchable framework configured to extend across the hinge joint of the area of the body when the support is secured to the area of the body, the framework having a surface for abutment with the area of the body including the hinge joint, and the framework comprising an integrally molded network of interconnected, elastomeric segments defining a plurality of permanent openings, and a structural hinge mechanism affixed to a first side of the framework, the structural hinge mechanism. The structural hinge mechanism includes a strut component, a first arm component connected to the strut component such that the first arm component is rotatable relative to the strut component about a first pivot axis, and a second arm component connected to the strut component such that the second arm component is rotatable relative to the strut component about a second pivot axis. The strut component is configured to extend with the framework across the hinge joint when the support is secured to the area of the body such that the first pivot axis is located on a first side of the hinge joint and the second pivot axis is located on a second, opposite side of the hinge joint. The support further includes a secondary hinge mechanism affixed to a second side of the framework opposite the first side of the framework. The structural hinge mechanism is larger than the secondary hinge mechanism so as to bias the application of pressure towards one side of the hinge joint when the support is secured to the area of the body. Further, the elastomeric segments of the framework are designed in such a way as to asymmetrically assert pressure on the hinge joint when the support is secured to the area of the body.

In a feature of this aspect, the flexible framework is configured to be stretched and tensioned into abutment with the area of the body such that the flexible framework conforms to the shape and contour of the area of the body when stretched and tensioned, the flexible framework having a relaxed state when not stretched and tensioned in which the flexible framework does not conform to the shape and contour of the area of the body.

In a feature of this aspect, one of the permanent openings comprises an alignment opening configured to receive a portion of the hinge joint.

In a feature of this aspect, the secondary hinge mechanism comprises a strut component, a first arm component connected to the strut component such that the first arm component is rotatable relative to the strut component about a third pivot axis, and a second arm component connected to the strut component such that the second arm component is rotatable relative to the strut component about a fourth pivot axis, and the strut component is configured to extend with the framework across the hinge joint when the support is secured to the area of the body such that the third pivot axis is located on the first side of the hinge joint and the fourth pivot axis is located on the second, opposite side of the hinge joint. In one or more implementations, the strut component of the secondary hinge mechanism is at least partially embedded in a material of the framework. In one or more implementations, each of the first and second arm components of the secondary hinge mechanism is at least partially embedded in a material of the framework. In one or more implementations, the support further includes first, second, third, and fourth strap interface components, the first strap interface component being connected to the first arm component of the structural hinge mechanism and defining at least one opening therein configured to receive therethrough a strap for attachment of the framework to the body on the first side of the hinge joint, the second strap interface component being connected to the second arm component of the structural hinge mechanism and defining at least one opening therein configured to receive therethrough a strap for attachment of the framework to the body on the second side of the hinge joint, and the third and fourth strap interface components being connected to arm components of the secondary hinge mechanism. In one or more implementations, the support further includes first, second, third, and fourth strap openings configured to receive therethrough a strap for attachment of the framework to the body. In one or more implementations, the support includes first, second, third, and fourth strap interface components, the first strap interface component being connected to the first arm component of the structural hinge mechanism and defining at least one opening therein configured to receive therethrough a strap for attachment of the framework to the body on the first side of the hinge joint, the second strap interface component being connected to the second arm component of the structural hinge mechanism and defining at least one opening therein configured to receive therethrough a strap for attachment of the framework to the body on the second side of the hinge joint, the third strap interface component being connected to the first arm component of the secondary hinge mechanism and defining at least one opening therein configured to receive therethrough a strap for attachment of the framework to the body on the first side of the hinge joint, and the fourth strap interface component being connected to the second arm component of the secondary hinge mechanism and defining at least one opening therein configured to receive therethrough a strap for attachment of the framework to the body on the second side of the hinge joint.

In a feature of this aspect, the secondary hinge mechanism comprises a stay.

In a feature of this aspect, the framework includes a plurality of transverse members curving generally towards a middle portion of the second side of the framework the secondary hinge mechanism is affixed to.

In a feature of this aspect, one of the permanent openings comprises an alignment opening configured to receive a portion of the hinge joint, a first side of the alignment opening proximate the structural hinge mechanism being generally larger than a second side of the alignment opening proximate the secondary hinge mechanism.

In a feature of this aspect, one of the permanent openings comprises an alignment opening configured to receive a portion of the hinge joint, a height of the alignment opening proximate the structural hinge mechanism being generally larger than a height of the alignment opening proximate the secondary hinge mechanism.

In a feature of this aspect, the framework is configured such that it is capable of lying generally flat when the support is not secured to the area of the body Another aspect relates to a support for an area of a body that includes a hinge joint. The support includes a flexible, elastically stretchable framework configured to extend across the hinge joint of the area of the body when the support is secured to the area of the body, the framework having a surface for abutment with the area of the body including the hinge joint, and the framework comprising an integrally molded network of interconnected, elastomeric segments defining a plurality of permanent openings; a structural hinge mechanism affixed to a first side of the framework, the structural hinge mechanism comprising a strut component, a first arm component connected to the strut component such that the first arm component is rotatable relative to the strut component about a first pivot axis, and a second arm component connected to the strut component such that the second arm component is rotatable relative to the strut component about a second pivot axis, wherein the strut component is configured to extend with the framework across the hinge joint when the support is secured to the area of the body such that the first pivot axis is located on a first side of the hinge joint and the second pivot axis is located on a second, opposite side of the hinge joint; wherein the elastomeric segments of the framework are designed in such a way as to asymmetrically assert pressure on the hinge joint when the support is secured to the area of the body.

In a feature of this aspect, the support further includes a second hinge mechanism affixed to a second side of the framework opposite the first side of the framework. In at least some implementations, the second hinge mechanism comprises a structural hinge. In at least some implementations, the second hinge mechanism comprises a bi-centric hinge mechanism. In at least some implementations, the second hinge mechanism is the same size as the structural hinge mechanism. In at least some implementations, the support further includes a flexible stay disposed at a second side of the framework opposite the first side of the framework.

Another aspect relates to an apparatus. The apparatus comprises a clothing article for an area of a body that includes a hinge joint, a flexible, elastically stretchable framework secured to the clothing article so as to extend across a hinge joint of the area of the body when the clothing article is worn, the framework comprising an integrally molded network of interconnected, elastomeric segments defining a plurality of permanent openings, and a structural hinge mechanism affixed to a first side of the framework. The structural hinge mechanism includes a strut component, a first arm component connected to the strut component such that the first arm component is rotatable relative to the strut component about a first pivot axis, and a second arm component connected to the strut component such that the second arm component is rotatable relative to the strut component about a second pivot axis, wherein the strut component is configured to extend with the framework across the hinge joint when the support is secured to the area of the body such that the first pivot axis is located on a first side of the hinge joint and the second pivot axis is located on a second, opposite side of the hinge joint. The elastomeric segments of the framework are designed in such a way as to asymmetrically assert pressure on the hinge joint when the clothing article is worn.

Another aspect relates to a support for an area of a body that includes a hinge joint. The support includes a flexible, elastically stretchable framework configured to extend across the hinge joint of the area of the body when the support is secured to the area of the body, the framework having a surface for abutment with the area of the body including the hinge joint, and the framework comprising an integrally molded network of interconnected, elastomeric segments defining a plurality of permanent opening, and a structural hinge mechanism affixed to a first side of the framework. The structural hinge mechanism includes a strut component, a first arm component connected to the strut component such that the first arm component is rotatable relative to the strut component about a first pivot axis, and a second arm component connected to the strut component such that the second arm component is rotatable relative to the strut component about a second pivot axis. The strut component is configured to extend with the framework across the hinge joint when the support is secured to the area of the body such that the first pivot axis is located on a first side of the hinge joint and the second pivot axis is located on a second, opposite side of the hinge joint. The support further includes a secondary hinge mechanism affixed to a second side of the framework opposite the first side of the framework. The structural hinge mechanism is larger than the secondary hinge mechanism so as to bias the application of pressure towards one side of the hinge joint when the support is secured to the area of the body, and the elastomeric segments of the framework are designed in such a way as to asymmetrically assert pressure on the hinge joint when the support is secured to the area of the body. The framework is configured such that it is capable of lying generally flat when the support is not secured to the area of the body.

In a feature of this aspect, the flexible framework is configured to be stretched and tensioned into abutment with the area of the body such that the flexible framework conforms to the shape and contour of the area of the body when stretched and tensioned, the flexible framework having a relaxed state when not stretched and tensioned in which the flexible framework does not conform to the shape and contour of the area of the body.

In a feature of this aspect, the secondary hinge mechanism comprises a strut component, a first arm component connected to the strut component such that the first arm component is rotatable relative to the strut component about a third pivot axis, and a second arm component connected to the strut component such that the second arm component is rotatable relative to the strut component about a fourth pivot axis, and the strut component is configured to extend with the framework across the hinge joint when the support is secured to the area of the body such that the third pivot axis is located on the first side of the hinge joint and the fourth pivot axis is located on the second, opposite side of the hinge joint.

In a feature of this aspect, the secondary hinge mechanism comprises a stay.

In a feature of this aspect, the framework includes a plurality of transverse members curving generally towards a middle portion of the second side of the framework the secondary hinge mechanism is affixed to.

In a feature of this aspect, one of the permanent openings comprises an alignment opening configured to receive a portion of the hinge joint, a first side of the alignment opening proximate the structural hinge mechanism being generally larger than a second side of the alignment opening proximate the secondary hinge mechanism.

In a feature of this aspect, one of the permanent openings comprises an alignment opening configured to receive a portion of the hinge joint, a height of the alignment opening proximate the structural hinge mechanism being generally larger than a height of the alignment opening proximate the secondary hinge mechanism.

Another aspect relates to a support for an area of a body that includes a hinge joint. The hinge joint includes a flexible, elastically stretchable framework configured to extend across the hinge joint of the area of the body when the support is secured to the area of the body, the framework having a surface for abutment with the area of the body including the hinge joint, and the framework comprising an integrally molded network of interconnected, elastomeric segments defining a plurality of permanent openings, and a structural hinge mechanism affixed to a first side of the framework. The structural hinge mechanism includes a strut component, a first arm component connected to the strut component such that the first arm component is rotatable relative to the strut component about a first pivot axis, and a second arm component connected to the strut component such that the second arm component is rotatable relative to the strut component about a second pivot axis. The strut component is configured to extend with the framework across the hinge joint when the support is secured to the area of the body such that the first pivot axis is located on a first side of the hinge joint and the second pivot axis is located on a second, opposite side of the hinge joint. The support further includes a secondary hinge mechanism affixed to a second side of the framework opposite the first side of the framework, the secondary hinge mechanism comprising a strut component, a first arm component connected to the strut component such that the first arm component is rotatable relative to the strut component about a third pivot axis, and a second arm component connected to the strut component such that the second arm component is rotatable relative to the strut component about a fourth pivot axis. The strut component is configured to extend with the framework across the hinge joint when the support is secured to the area of the body such that the third pivot axis is located on the first side of the hinge joint and the fourth pivot axis is located on the second, opposite side of the hinge joint. The structural hinge mechanism is larger than the secondary hinge mechanism so as to bias the application of pressure towards one side of the hinge joint when the support is secured to the area of the body, and the elastomeric segments of the framework are designed in such a way as to asymmetrically assert pressure on the hinge joint when the support is secured to the area of the body. One of the permanent openings comprises an alignment opening configured to receive a portion of the hinge joint, a first side of the alignment opening proximate the structural hinge mechanism being generally larger than a second side of the alignment opening proximate the secondary hinge mechanism.

In one or more preferred implementations, an area of the body a support is configured for comprises two hinge joints.

Another aspect relates to a support for an area of a body that includes a hinge joint comprising a flexible, elastically stretchable framework configured to extend across the hinge joint of the area of the body when the support is secured to the area of the body, the framework having a surface for abutment with the area of the body including the hinge joint, and the framework comprising an integrally molded network of interconnected, elastomeric segments defining a plurality of permanent openings; a hinge mechanism affixed to a first side of the framework, wherein the hinge mechanism is configured to extend with the framework across the hinge joint when the support is secured to the area of the body; and wherein the elastomeric segments of the framework are designed in such a way as to asymmetrically assert pressure on the hinge joint when the support is secured to the area of the body.

In a feature of this aspect, the hinge mechanism comprises two struts and one pivot point.

In a feature of this aspect, the hinge mechanism includes more than two pivot points.

In a feature of this aspect, the hinge mechanism includes a flexible strut.

In a feature of this aspect, the hinge mechanism comprises a simple hinge.

In a feature of this aspect, the hinge mechanism comprises a flexible stay.

In a feature of this aspect, the hinge mechanism comprises a stiffening member.

In a feature of this aspect, the framework wraps more than 180 degrees around the hinge joint.

In a feature of this aspect, the framework wraps 360 degrees around the hinge joint.

Another aspect relates to a support for an area of a body that includes a hinge joint comprising a flexible, elastically stretchable framework configured to extend across the hinge joint of the area of the body when the support is secured to the area of the body, the framework having a surface for abutment with the area of the body including the hinge joint, and the framework comprising an integrally molded network of interconnected, elastomeric segments defining a plurality of permanent openings; a stiffening member affixed to the framework; wherein the elastomeric segments of the framework are designed in such a way as to asymmetrically assert pressure on the hinge joint when the support is secured to the area of the body.

In a feature of this aspect, the stiffening member extends across a back of the hinge joint.

In a feature of this aspect, the stiffening member extends across a front of the hinge joint.

In a feature of this aspect, the stiffening member extends from one side of the hinge joint to the other.

In a feature of this aspect, the support includes two stiffening members, one disposed on each side of the support, that are contiguous with one another.

In a feature of this aspect, the support includes two stiffening members, one disposed on each side of the support, that are continuous with one another.

In a feature of this aspect, the stiffening member comprises a hinge mechanism.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
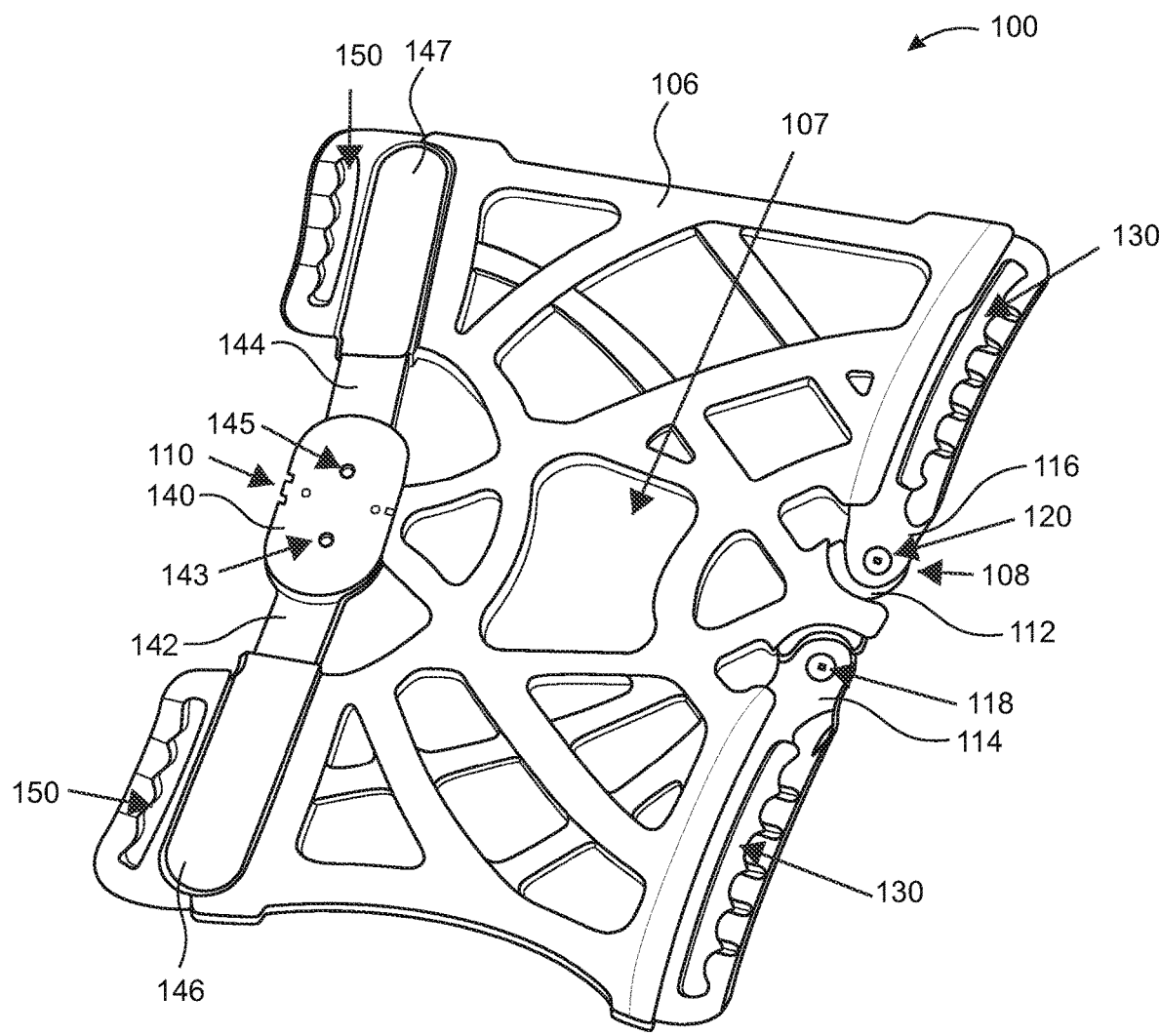
FIG. 1 illustrates a support in accordance with a preferred implementation.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

FIG. 1 illustrates a biased support 100 configured for an area of a body having a hinge joint. The support 100 includes a flexible, elastically stretchable framework 106 that is configured to extend across the hinge joint of the area of the body. With reference to support 100, this support is intended and designed for use with the area of a person's knee, and the flexible, elastically stretchable framework 106 is configured to extend across and encompass the knee.

The flexible framework 106 comprises an elastomeric material and, specifically, the framework 106 defines a flexible, elastically stretchable web of elastomeric interconnected members. The elastomeric interconnected members mostly comprise generally linear or curved segments. Furthermore, the framework 106, and the interconnected members in particular, preferably include no internal cavities or pockets of either fluid or gas. The interconnected members define a plurality of permanent openings in the web that extend completely through the framework 106. The openings are "permanent" in that they exist regardless of whether the framework 106 actually is disposed in abutment with the body due to the permanent interconnection of the segments defining the openings. Furthermore, some of these openings are completely bounded by the interconnected members, and the interconnected members defining such an opening constitute a portion of the framework 106 that is stretchable and recoverable about the entire boundary of the opening with the framework 106.

The web includes a larger opening that is symmetrically oriented with respect to the side edges of the framework 106 and that is configured to receive a portion of the knee therethrough and which serves as an alignment opening 107. Specifically, the alignment opening 107 is defined and bounded completely by interconnected members of the framework 106 and is dimensioned and shaped specifically to receive a joint protuberance of the knee. For example, insofar as the framework 106 is adapted to abut a lower thigh and upper calf of a human leg, the alignment opening 107 is shaped to receive the patella of the knee of the leg.

The framework 106 is configured to be stretched and tensioned into abutment with the area of the knee such that the framework 106 conforms to the shape and contour of the area of the knee when stretched and tensioned. In particular, the framework 106 has a relaxed state when not stretched and tensioned as shown, for example, in FIG. 1. In this state, the framework 106 does not conform to the shape and contour of the area of the knee.

It will be appreciated by an Ordinary Artisan that, due to the elastically stretchable nature of the framework, the support allows flexing of a hinge joint of the body and, in fact, contributes to such flexing. In this regard, because at least portions of the framework 106 are elastically stretchable, flexing of the knee from an extended position to a retracted or bent position results in the expansion of the framework 106 and storage of potential energy therein that is released as kinetic energy when the knee is returned to the extended position. The support 100 thus is not an immobilizing support but, instead, the support 100 is a potentiating support for the area of the body including the knee joint insofar as the framework 106 is capable of dynamically biasing a joint toward a particular state of extension or flexion.

In particular, because of the elastically stretchable and recoverable nature of the material of the framework 106, the framework 106 stores potential energy when stretched and tensioned that is released as kinetic energy upon transitioning of the framework 106 back toward a relaxed (or less tensioned) state. This correlates to transitioning of hinge mechanisms 108, 110 (discussed next) from a first position corresponding to a flexed or bent position of the knee, to a second position of the hinge mechanisms 108, 110 corresponding to a less flexed or bent (i.e., more extended) position of the knee.

The support 100 further includes a pair of hinge mechanism 108, 110. Each hinge mechanism 108, 110 is affixed to the framework 106. As can be seen in FIG. 1, the hinge mechanism 108 differs from the hinge mechanism 110. The hinge mechanism 110 can be characterized as a structural hinge mechanism, and is larger than the hinge mechanism 108, which can be characterized as a secondary hinge mechanism, so as to bias the application of pressure towards one side of the hinge joint when the support 100 is secured to a user's body. This biased application of pressure is further reinforced by the shape of the framework, which is designed, as illustrated in FIG. 1, in such a way as to asymmetrically assert pressure on a user's knee when the support 100 is secured to the user's body.

Hinge mechanism 108 includes a strut component 112 and first and second arm components 114, 116. Each of these components preferably is generally planar.

The first arm component 114 is connected to the strut component 112 such that the first arm component 114 is rotatable relative to the strut component 112 about a first pivot axis 118. As opposed to, for example, a continuous hinge, the strut component 112 and the first arm component 114 are mechanically connected, and the first pivot axis 118 is fixed relative to each of these components. Consequently, the first arm component 114 is rotatable relative to the strut component 112 only about a first pivot axis 118.

Similar to the first arm component 114, the second arm component 116 is connected to the strut component 112 such that the second arm component 116 is rotatable relative to the strut component 112 about a second pivot axis 120. Moreover, the strut component 112 and the second arm component 116 are mechanically connected, and the second pivot axis 118 is fixed relative to each of these components. Consequently, the second arm component 116 is rotatable relative to the strut component 112 only about the second pivot axis 120.

The hinge mechanism 108 is located along a first side edge of the framework 106, and the hinge mechanism 110 is located along a second, opposite side edge of the framework 106. The hinge member 108, and the strut component 112 in particular, is partially embedded in a material of the framework 106. Indeed, in one or more preferred implementations, a material of the framework 106 actually encompasses and completely encircles a middle portion of the strut component 112. The strut component 112 may be so embedded within the material of the framework during the manufacture of the support by molding or otherwise forming the framework 106 directly onto the strut component 112. Similarly, each of the first and second arm components 114, 116 may be at least partially embedded in a material of the framework 106.

With further regard to hinge mechanism 108, a first hinging member connects the first arm component 114 to the strut component 112, the first hinging member 122 including a cylindrical portion in abutment with which the first arm component 114 and strut component 112 rotate. Likewise, a second hinging member connects the second arm component 116 to the strut component 112, the second hinging member including a cylindrical portion in abutment with which the second arm component 116 and strut component 112 rotate. As will be appreciated, the first pivot axis 118 axially extends through the cylindrical portion of the first hinging member, and the second pivot axis 120 axially extends through the cylindrical portion of the second hinging member.

Each of the arm components 112, 114 includes a strap opening 130 defined therethrough that is designed for use with a strap. The portions of the arm components 112, 114 defining a strap opening 130 preferably include ridges for frictionally engaging one or more straps passing through the strap opening 130, as illustrated in FIG. 1.

The structural hinge mechanism 110 is similar to the secondary hinge mechanism 108 in that it comprises a bi-centric hinge, but, as noted above, the structural hinge mechanism 110 is larger than the secondary hinge mechanism 108 so as to bias the application of pressure towards one side of the hinge joint when the support 100 is secured to a user's body.

The structural hinge mechanism 110 comprises an enlarged hinge member 140, first and second arm components 142, 144 rotatably secured thereto so as to rotate about respective first and second pivot axes 143, 145, as illustrated in FIG. 1.

The support 100 further includes securement portions 146, 147 associated with the first and second arm components 142, 144. These securement portions 146, 147 may be attached to, overmolded over, or integrally formed with the first and second arm components 142, 144. In one or more preferred implementations, these securement portions 146, 147 are at least partially embedded in the framework 106. In one or more preferred implementations, however, the framework 106 may be partially embedded in the securement portions 146, 147. In one or more preferred implementations, the framework 106 and securement portions 146, 147 may alternatively or additionally be secured to one another in one or more other ways.

The securement portions 146, 147 each include a strap opening 150 defined therethrough that is designed for use with a strap. The portions of the securement portions 146, 147 defining a strap opening 150 preferably include ridges for frictionally engaging one or more straps passing through the strap opening 150, as illustrated in FIG. 1.

Each hinge mechanism 108, 110 is arranged relative to the framework 106 such that the hinge mechanism extends with the framework across the hinge joint such that one pivot axis of each hinge mechanism 108, 110 is located generally proximate or on one side of the hinge joint and the second pivot axis of each hinge mechanism 108, 110 is located generally proximate or on the other, opposite side of the hinge joint when the support is worn.

Preferably, the components of each hinge mechanism are rigid, in that each provides a degree of rigidity in a local area of the framework 106, especially proximate a local peripheral area along longitudinal sides of the framework 106 within which such respective component may be attached and/or embedded or otherwise may be affixed.

As noted above, the strap openings 130, 150 are configured to receive therethrough a strap for attachment of the framework 106 to an area of a user's body proximate the knee.

Figure 2:
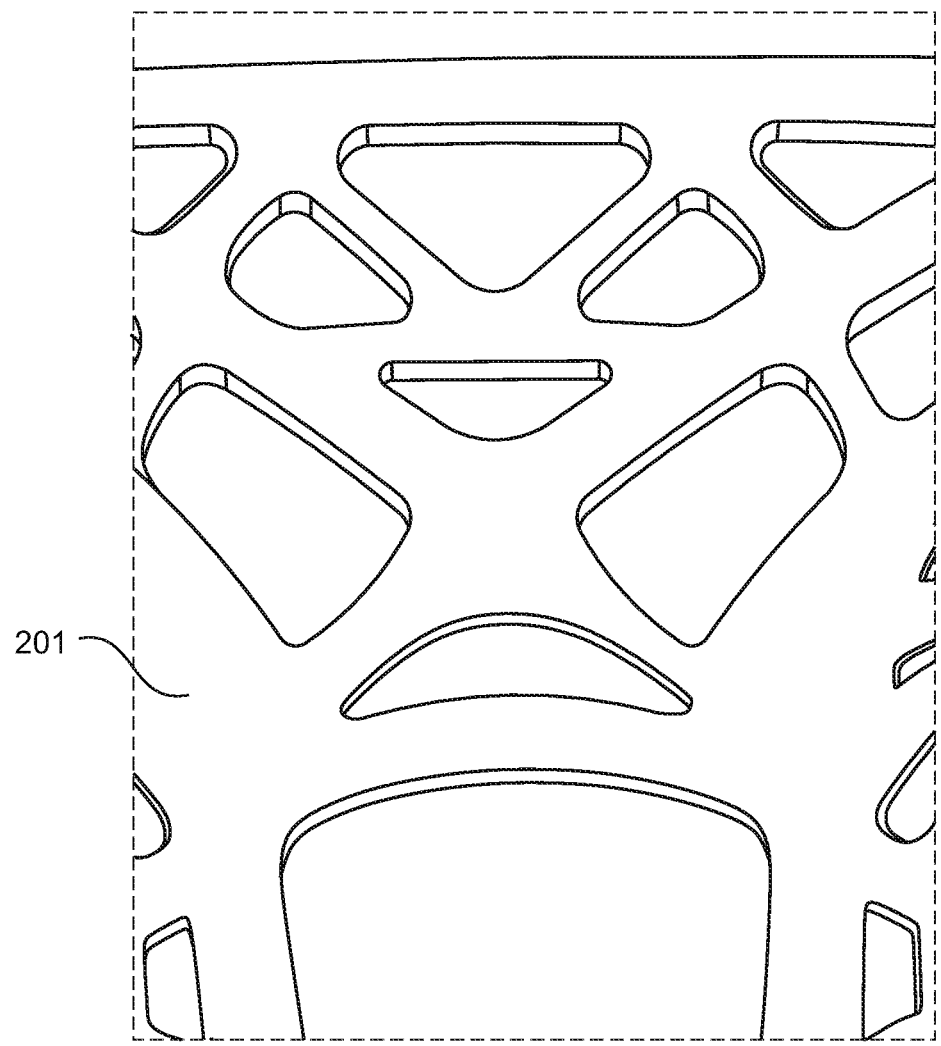
FIG. 2 illustrates exemplary protuberances of a framework of a support.

The front side of the framework 106 as shown in FIG. 1 generally is the same as the back side of the framework 106; however, unlike the surface of the front side of the framework 106, selected areas of the surface of the back side of the framework 106 include raised protuberances, which protuberances are intended to increase the frictional abutment of the framework 106 with the area of the knee when the support 106 is donned. The protuberances 138 serve to position and hold the support in abutment with the area of the body including the hinge joint. FIG. 2 illustrates exemplary such protuberances 201 on the back side of another framework.

In use of the support 100, the support 100 is positioned against the body such that the support 100 extends across the knee and such that the first pivot axes of the first and second hinge mechanisms are located generally proximate a top of, or above, the knee joint and the second pivot axes of the first and second hinge mechanisms are located generally proximate a bottom of, or below, the knee joint. The support 100 is further positioned such that the first and second hinge mechanisms extend on opposite sides of the hinge joint of the body. The positioning of the support 100 includes tensioning the framework 106 in abutment with the area of the knee and fastening the support 100 to the body on opposite sides of the knee such that the framework 106 is held in tension in its abutment with the area of the body including the knee. In so doing, the elastically stretchable framework 106 preferably conforms to the surface contour of the area of the knee as a result of the tensioning.

The support 100 is fastened to the body in a conforming position via a fastening mechanism (not shown in FIG. 1) that is detachably connected to and applies tension at different points of attachment to the framework 106 such that the framework 106 is expanded and tensioned in its abutment with the area of the body and, in particular, in the area of the knee. Furthermore, the fastening mechanism preferably comprises fastening straps with hook and loop fasteners. The straps are received and extend through the strap openings 130, 150 of the support 100.

The straps apply tension at different points of attachment to the framework 106 such that the framework 106 is expanded and tensioned in its abutment with the area of the body and, in particular, with the area of the knee. In particular, fastening straps are grasped and manually pulled at desired levels of tension, whereby the support 100 is highly adjustable. The resulting tensional forces from the straps are applied at multiple points of attachment along the opposite sides of the framework 106, whereby the framework 106 is elastically stretched and the surface thereof is shaped to fit the abutted area of the body including the knee. Preferably, the framework 106 of the support 100 does not overlap itself when worn.

The combination of the support 100 and fastening mechanism is referred to herein as a support assembly. A support assembly optionally may include a sleeve having an open-ended tubular structure. Such a sleeve preferably would extend around and completely encircle a leg and would be constructed of a soft material. The sleeve itself also may be elastically stretchable. Exemplary materials include synthetic and natural fabrics, monolayer and multi-layered textiles, woven and non-woven planar materials, neoprene bonded to fabric, spandex and elastane, felt, and natural and synthetic chamois. At least a portion of the sleeve would be disposed between the framework and a portion of the leg proximate the knee and would thereby serve as a liner for the framework.

A support assembly utilizing a different type of support is illustrated in FIGS. 3-7. Although the support illustrated in FIGS. 3-7 is not configured to bias the application of pressure towards one side of a user's hinge joint when the support is secured to the user's body, the figures and accompanying discussion are included to illustrate use of a fastening mechanism and sleeve which might be utilized in combination with the support 100, which is configured to bias the application of pressure towards one side of a wearer's hinge joint.

Figure 3:
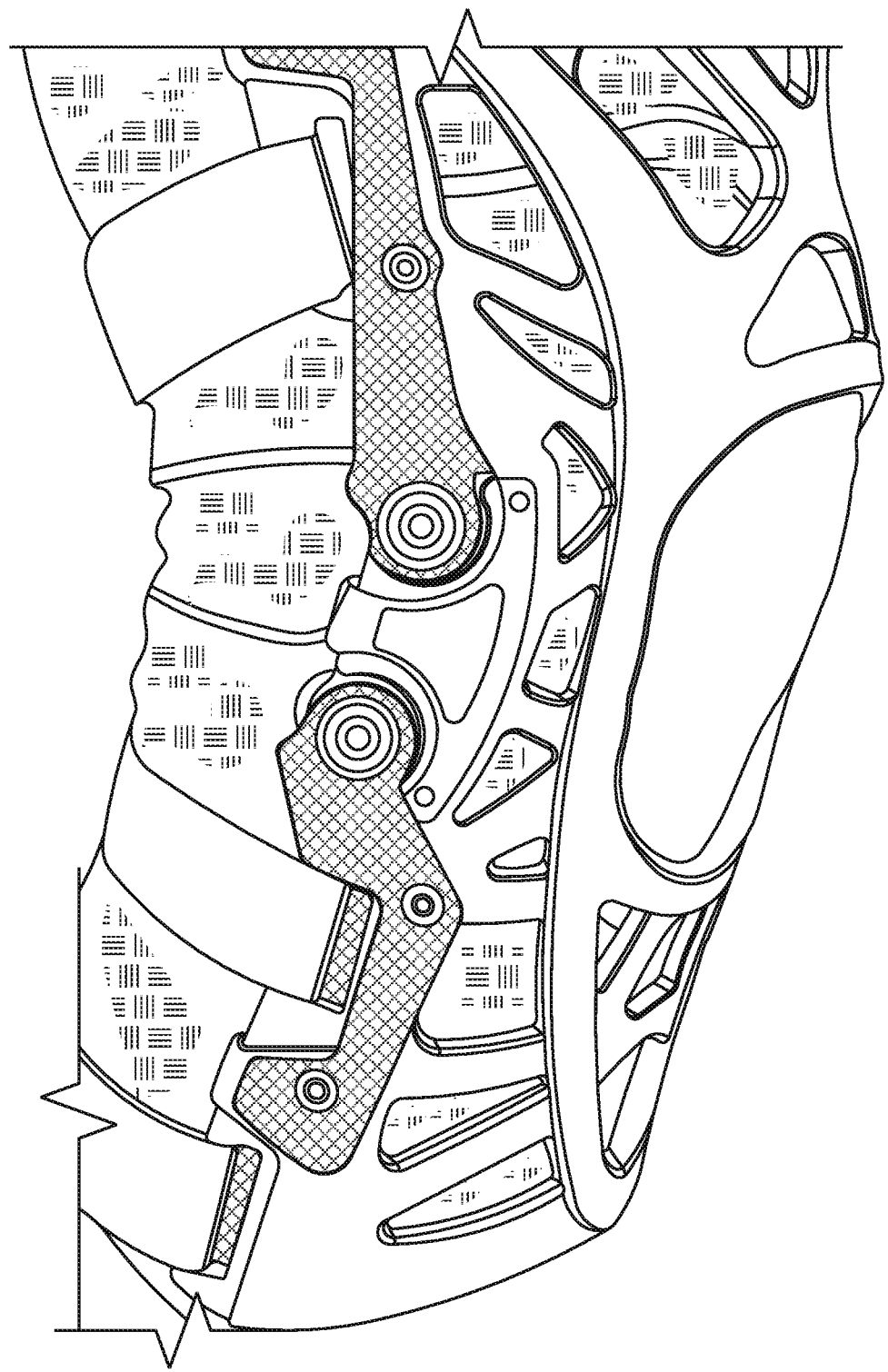
FIG. 3 is a side perspective view of a support assembly being worn.
Figure 4:
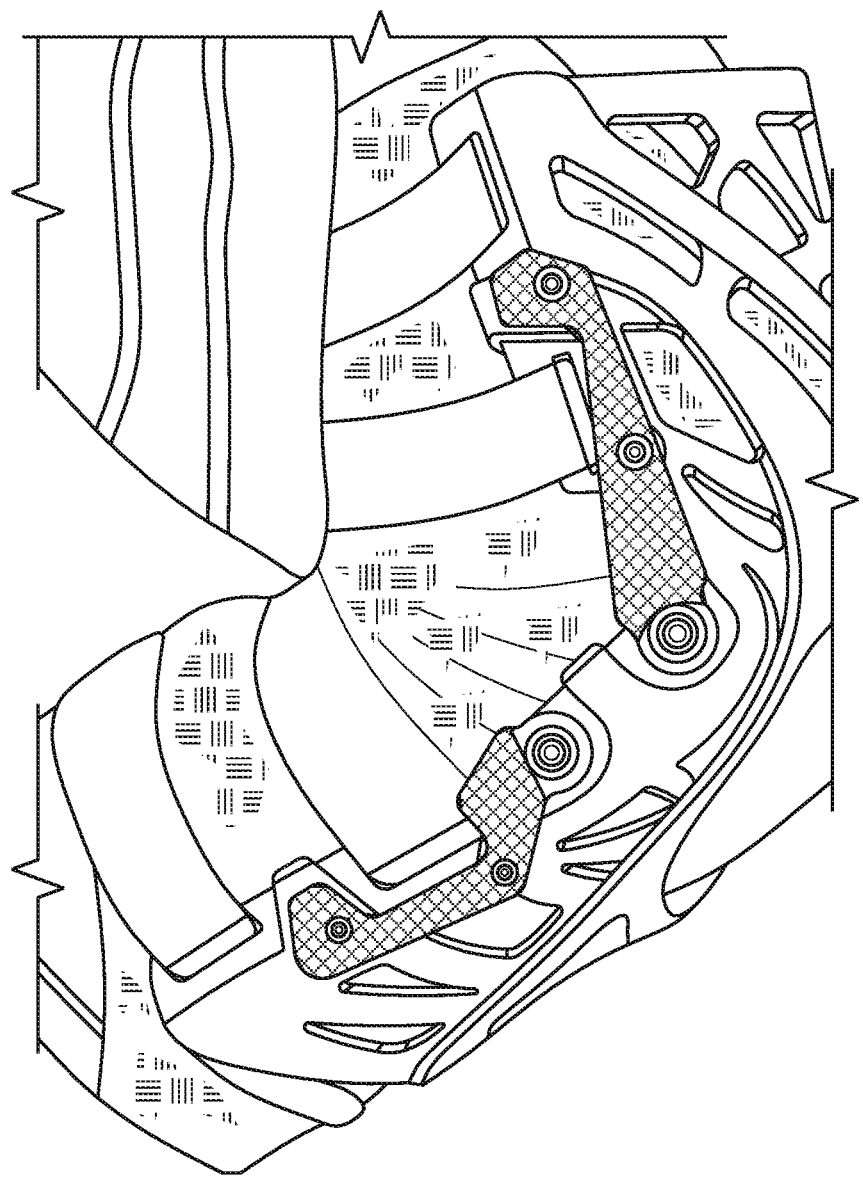
FIG. 4 is another side perspective view of the support assembly of FIG. 3 being worn.
Figure 5:
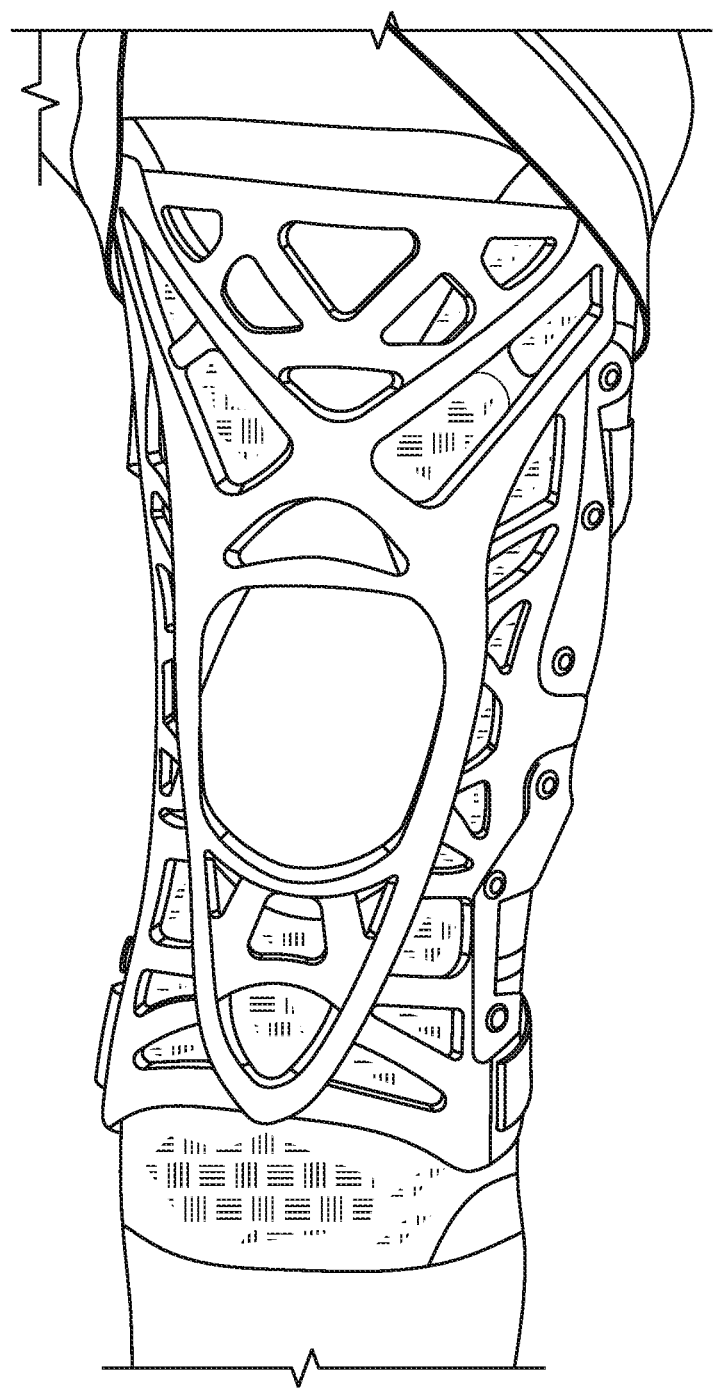
FIG. 5 is a perspective view of a front of the support assembly of FIG. 3 being worn.
Figure 6:
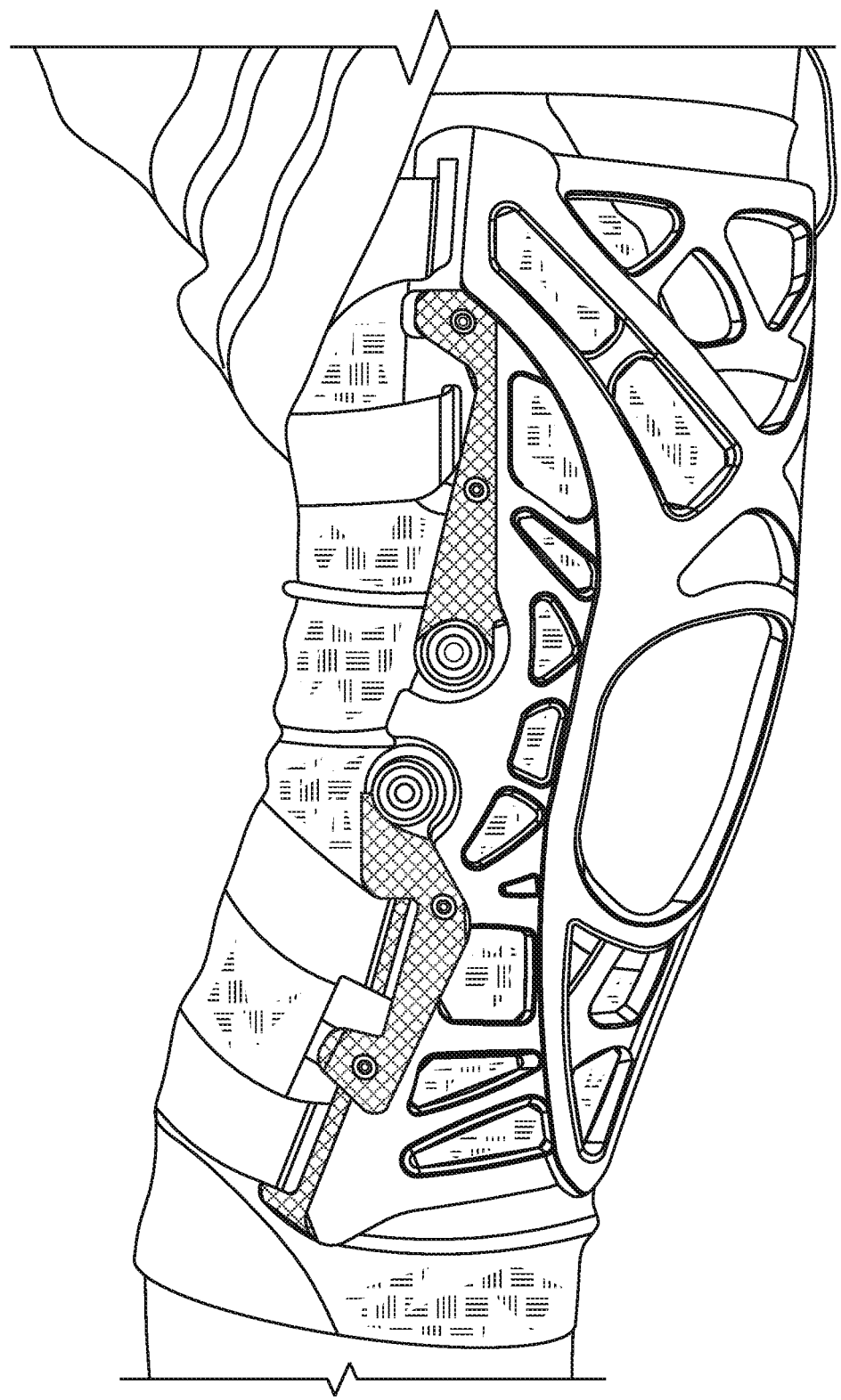
FIG. 6 is another side perspective view of the support assembly of FIG. 3 being worn.
Figure 7:
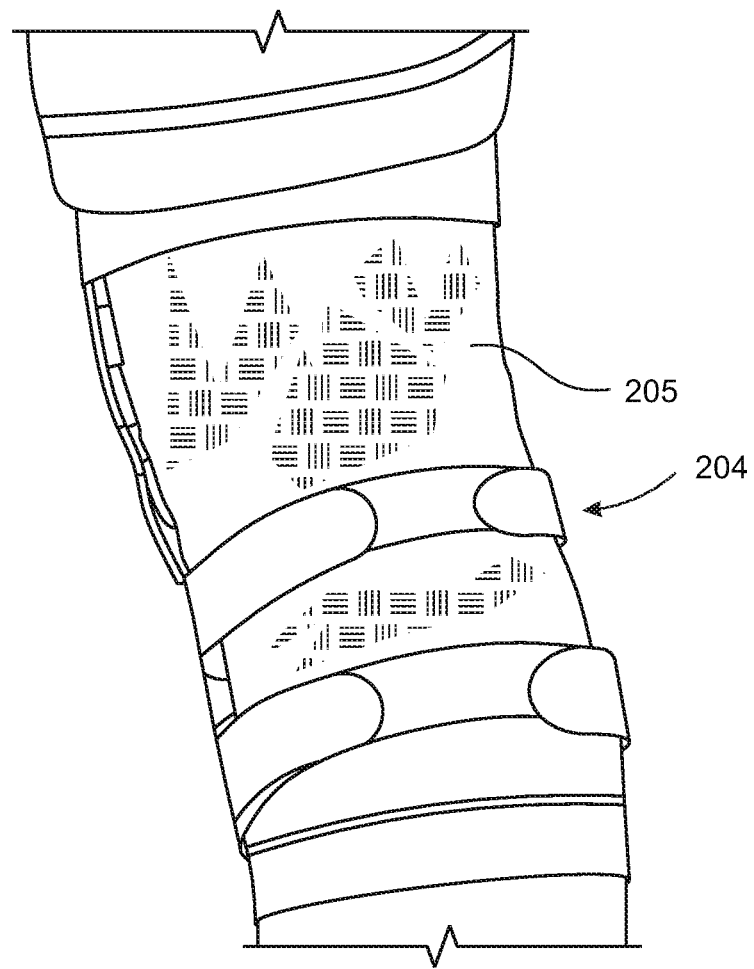
FIG. 7 is a perspective view of the rear of the support assembly of FIG. 3 being worn.

In this regard, FIG. 3 is a side perspective view of a support assembly being worn; FIG. 4 is another side perspective view of the support assembly being worn; FIG. 5 is a perspective view of a front of the support assembly being worn; FIG. 6 is another side perspective view of the support assembly being worn; and FIG. 7 is a perspective view of the rear of the support assembly being worn.

The support assembly includes a support and a fastening mechanism 204 as well as a sleeve 205 (best seen in FIG. 7) that serves as a liner for the framework of the support.

The support assembly may be configured as disclosed in U.S. Pat. No. 7,691,074 or USPA Pub. No. 2009/0259156, which are both hereby incorporated herein by reference, e.g. may be configured to utilize one or more fastening mechanisms as disclosed in such incorporated references.

Although the illustrated and described support 100 includes two bi-centric hinge mechanisms disposed opposite one another, namely the structural hinge mechanism 110 and the secondary hinge mechanism 108, in one or more preferred implementations a support only includes a single structural hinge mechanism that is disposed on one side of the support. In one or more preferred implementations, the other side of the support simply includes a flexible stay. In one or more preferred implementations, a support includes two structural hinges. In at least some implementations, these structural hinges may even be the same size, with a framework of the support being designed to bias the application of pressure towards one side of a wearer's hinge joint when the support 100 is secured to the wearer's body. In one or more preferred implementations, a framework might not be so designed, and a structural hinge serves to bias application of pressure, for example in combination with a smaller hinge or flexible stay. As disclosed herein, in one or more preferred implementations, both a structural hinge and a framework are configured to bias application of pressure. In preferred implementations, the structural hinge mechanism and the framework work together to bias application of pressure generally in the same direction.

In one or more preferred implementations, a support includes one or more hinge mechanisms comprising two struts and one pivot. In one or more preferred implementations, a hinge mechanism includes more than two pivot points, and may include an extremely high number of pivot points. In one or more preferred implementations, a strut is flexible so as to potentially be characterized as including "infinite" pivot points. In one or more preferred implementations, a simple hinge is utilized. In one or more preferred implementations, a flexible stay is utilized on either side of a support, either with or without one or more hinge mechanisms.

Although described herein as including hinge mechanisms and components thereof (some of which can be characterized in at least some implementations as stiffeners) positioned at a medial or lateral position, or inside or outside, of a joint, in at least some preferred implementations a stiffener or hinge is positioned otherwise, for example, a stiffener or hinge might be positioned to wrap around in front of and/or behind a joint, or pass over or under a joint, and could be characterized as incorporating a back or front portion of a hinge joint. Further, in one or more preferred implementations a first stiffener or hinge might be contiguous or continuous from one side to another, e.g. a stiffener or hinge on a first side might extend to be contiguous or continuous with a stiffener or hinge on another side. Similarly, in one or more preferred implementations, a framework, or web, wraps around a hinge joint to a greater or lesser extent than that illustrated and described hereinabove. In at least some implementations a framework may even be contoured to correspond to an area of the body.

Figure 8:
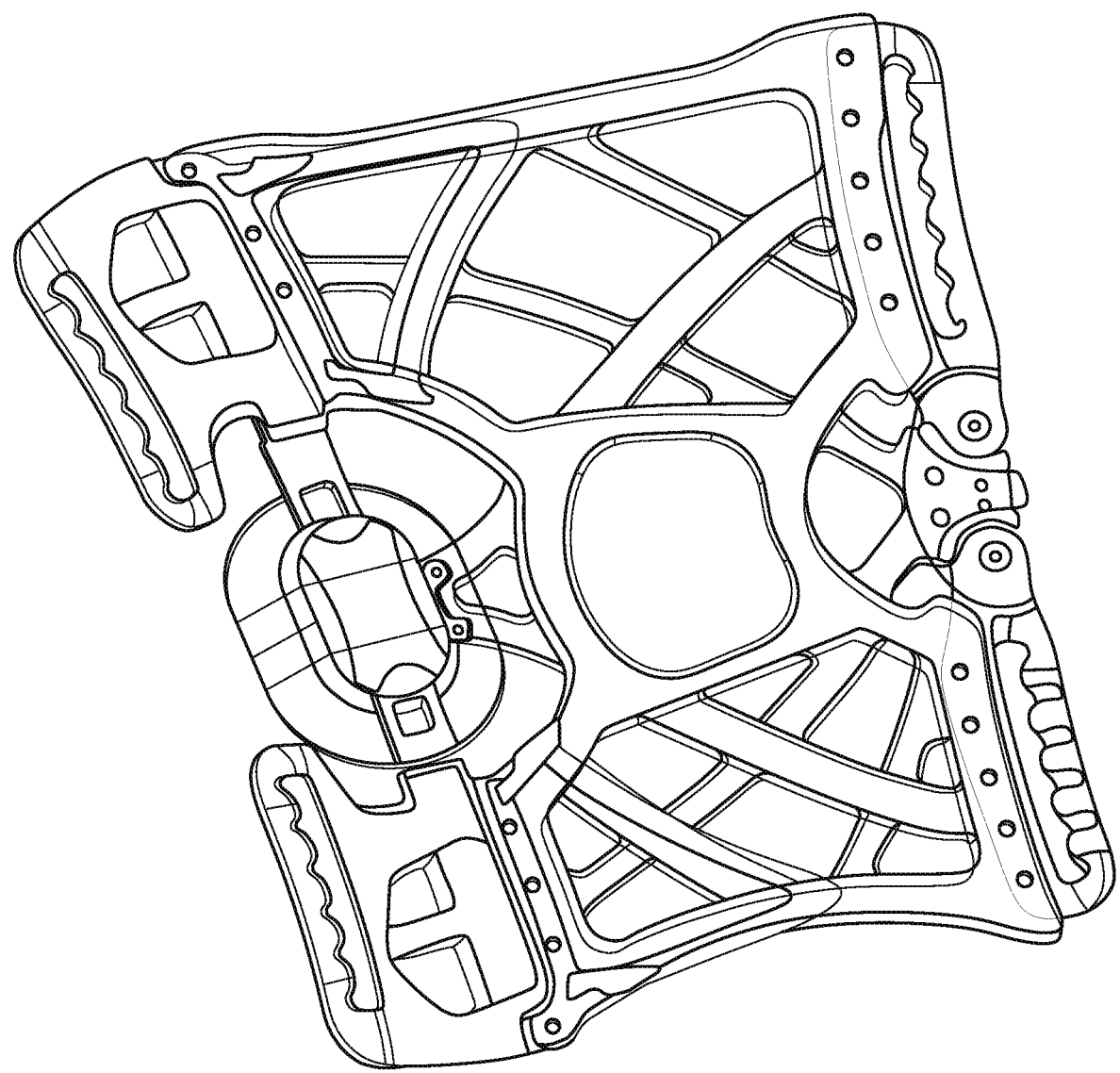
FIGS. 8 and 9 each illustrate an exemplary support in accordance with one or more preferred implementations.
Figure 9:
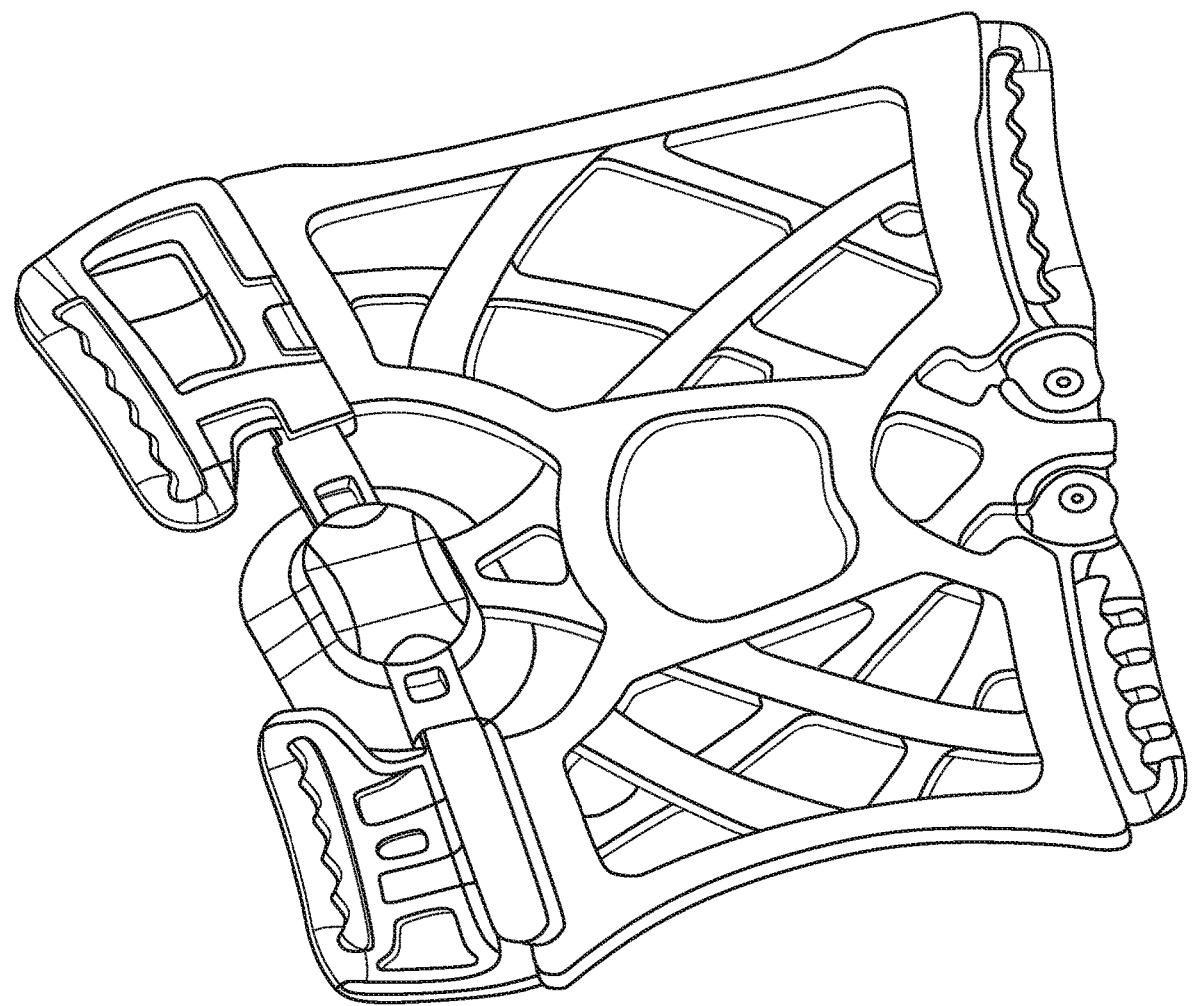

FIGS. 8 and 9 each illustrate an exemplary support in accordance with one or more preferred implementations.

In one or more preferred implementations, supports disclosed herein preferably are manufactured in injection molding processes, whereby the various components of each embodiment of the support, including, inter alia, the framework and strut components, are integrally formed from elastomeric materials. The injection molding processes preferably comprise, for each support, multi-step injection molding, whereby each component can be formed from different elastomeric materials having different elastic stretchability even though the components are integrally constructed.

In particular, some or all of the hinge mechanism components can be formed through injection molding of one or more first elastomeric materials, and then the framework can be formed through injection molding of a second elastomeric material about some or all of the hinge mechanism components. This is particularly useful in manufacturing embodiments having hinge mechanism components that are intended to provide a degree of rigidity to side areas of the framework, which can be readily made in an efficient and cost effective manner.

Additionally, the framework may be made of differing elastomeric materials and/or selected groups of interconnected segments of the framework can be made with varying thickness thereby providing different elastic characteristics and, thereby, providing different resistances to stretching in such areas.

While the foregoing supports in accordance with preferred embodiments of the invention relate to potentiating supports for the area of the body including the knee, other supports within the scope of the invention are similarly designed but are intended for use in, and are configured for, the area of the elbow, or even other areas. Other implementations may include clothing having one or more expandable and recoverable frameworks with or without one or more hinging mechanisms.

The supports disclosed herein are believed useful for injury treatment or prevention, rehabilitation, and motion enhancement. For example, these potentiating supports for the knee provide a secure fitting and comfortable knee brace for the purposes of supporting knee alignment, comfort, and protection in the activities of daily living, athletics, and working and in the treatment or rehabilitation of an injured or ailing knee, all the while providing joint motion assistance for performance enhancement in everyday and athletic activities. In this regard, potential energy is stored and returned for use to assist the body in its natural knee movement in a preferred knee support of the present invention.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A support for an area of a body that includes a hinge joint comprising:
   (a) a flexible, elastically stretchable framework configured to extend across the hinge joint of the area of the body when the support is secured to the area of the body, the flexible, elastically stretchable framework having a surface for abutment with the area of the body including the hinge joint, and the flexible, elastically stretchable framework comprising an integrally molded network of interconnected, elastomeric segments defining a plurality of permanent openings;
   (b) a structural hinge mechanism affixed to a first side of the flexible, elastically stretchable framework, the structural hinge mechanism comprising
      (i) a strut component,
      (ii) a first arm component connected to the strut component such that the first arm component is rotatable relative to the strut component about a first pivot axis, and
      (iii) a second arm component connected to the strut component such that the second arm component is rotatable relative to the strut component about a second pivot axis,
      (iv) wherein the strut component is configured to extend with the flexible, elastically stretchable framework across the hinge joint when the support is secured to the area of the body such that the first pivot axis is located on a first side of the hinge joint and the second pivot axis is located on a second, opposite side of the hinge joint; and
   (c) a secondary hinge mechanism affixed to a second side of the flexible, elastically stretchable framework opposite the first side of the flexible, elastically stretchable framework;
   (d) wherein the structural hinge mechanism is larger than the secondary hinge mechanism so as to bias application of pressure towards one side of the hinge joint when the support is secured to the area of the body; and
   (e) wherein the elastomeric segments of the flexible, elastically stretchable framework are designed in such a way as to asymmetrically assert pressure on the hinge joint biased towards one side of the hinge joint when the support is secured to the area of the body.

2. The support of claim 1, wherein the secondary hinge mechanism comprises
   (i) a strut component,
   (ii) a first arm component connected to the strut component such that the first arm component is rotatable relative to the strut component about a third pivot axis,
   (iii) a second arm component connected to the strut component such that the second arm component is rotatable relative to the strut component about a fourth pivot axis, and
   (iv) wherein the strut component is configured to extend with the flexible, elastically stretchable framework across the hinge joint when the support is secured to the area of the body such that the third pivot axis is located on the first side of the hinge joint and the fourth pivot axis is located on the second, opposite side of the hinge joint.

3. The support of claim 2, wherein the strut component of the secondary hinge mechanism is at least partially embedded in a material of the flexible, elastically stretchable framework.

4. The support of claim 2, wherein each of the first and second arm components of the secondary hinge mechanism is at least partially embedded in a material of the flexible, elastically stretchable framework.

5. The support of claim 1, further comprising first, second, third, and fourth strap openings configured to receive therethrough a strap for attachment of the flexible, elastically stretchable framework to the body.

6. The support of claim 2, further comprising strap openings defined in each of the structural hinge mechanism and the secondary hinge mechanism.

7. The support of claim 1, wherein the flexible, elastically stretchable framework is configured to be stretched and tensioned into abutment with the area of the body such that the flexible, elastically stretchable framework conforms to a shape and contour of the area of the body when stretched and tensioned, the flexible elastically stretchable framework having a relaxed state when not stretched and tensioned in which the flexible elastically stretchable framework does not conform to the shape and contour of the area of the body.

8. The support of claim 1, wherein one of the permanent openings comprises an alignment opening configured to receive a portion of the hinge joint.

9. The support of claim 1, wherein the secondary hinge mechanism comprises a stay.

10. The support of claim 1, wherein the flexible, elastically stretchable framework includes a plurality of transverse members curving generally towards a middle portion of the second side of the flexible, elastically stretchable framework the secondary hinge mechanism is affixed to.

11. The support of claim 1, wherein one of the permanent openings comprises an alignment opening configured to receive a portion of the hinge joint, a first side of the alignment opening proximate the structural hinge mechanism being generally larger than a second side of the alignment opening proximate the secondary hinge mechanism.

12. The support of claim 1, wherein one of the permanent openings comprises an alignment opening configured to receive a portion of the hinge joint, a height of the alignment opening proximate the structural hinge mechanism being generally larger than a height of the alignment opening proximate the secondary hinge mechanism.

13. The support of claim 1, wherein the flexible, elastically stretchable framework is configured such that it is capable of lying generally flat when the support is not secured to the area of the body.

14. An apparatus comprising:
   (a) a clothing article for an area of a body that includes a hinge joint;
   (b) a flexible, elastically stretchable framework secured to the clothing article so as to extend across a hinge joint of the area of the body when the clothing article is worn, the flexible, elastically stretchable framework comprising an integrally molded network of interconnected, elastomeric segments defining a plurality of permanent openings; and
   (c) a structural hinge mechanism affixed to a first side of the flexible, elastically stretchable framework, the structural hinge mechanism comprising
      (i) a strut component,
      (ii) a first arm component connected to the strut component such that the first arm component is rotatable relative to the strut component about a first pivot axis, and (iii) a second arm component connected to the strut component such that the second arm component is rotatable relative to the strut component about a second pivot axis,
(iv) wherein the strut component is configured to extend with the flexible, elastically stretchable framework across the hinge joint when the clothing article is secured to the area of the body such that the first pivot axis is located on a first side of the hinge joint and the second pivot axis is located on a second, opposite side of the hinge joint;
(d) a secondary hinge mechanism affixed to a second side of the flexible, elastically stretchable framework opposite the first side of the flexible, elastically stretchable framework;
(e) wherein the structural hinge mechanism is larger than the secondary hinge mechanism so as to bias application of pressure towards one side of the hinge joint when the clothing article is worn; and
(f) wherein the elastomeric segments of the flexible, elastically stretchable framework are designed in such a way as to asymmetrically assert pressure on the hinge joint biased towards one side of the hinge joint when the clothing article is worn.

* * * * *